(12) United States Patent
Amin

(10) Patent No.: US 10,912,741 B2
(45) Date of Patent: Feb. 9, 2021

(54) PREVENTION OF LIVER CANCER WITH SAFRANAL-BASED FORMULATIONS

(71) Applicant: United Arab Emirates University, Al Ain (AE)

(72) Inventor: Amr Amin, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 16/288,930

(22) Filed: Feb. 28, 2019

(65) Prior Publication Data

US 2020/0276133 A1    Sep. 3, 2020

(51) Int. Cl.
*A61K 31/11* (2006.01)
*A61P 35/00* (2006.01)
*G01N 33/574* (2006.01)

(52) U.S. Cl.
CPC .............. *A61K 31/11* (2013.01); *A61P 35/00* (2018.01); *G01N 33/57438* (2013.01)

(58) Field of Classification Search
CPC ................................ A61K 31/11; A61P 35/00
See application file for complete search history.

(56) References Cited

PUBLICATIONS

Heindryckx et al. Int. J. Exp. Path., 2009, vol. 90, pp. 367-386 (Year: 2009).*
He et al. Oncotarget, 2015, vol. 6, No. 27, pp. 23306-23322 (Year: 2015).*
Farahmand et al. Biogerontology, 2013, vol. 14, pp. 63-71 (Year: 2013).*
Hosseinzadeh et al. DARU Journal of Pharmaceutical Sciences, 2015, vol. 23:31, pp. 1-9 (Year: 2015).*
Abdullaev FI & Espinosa-Aguirre JJ, "Biomedical properties of saffron and its potential use in cancer therapy and chemoprevention trials", PubMed, Cancer Detectection and Prevention, vol. 28, 2004, pp. 426-432, 7 pages.
Adimoolam et al., HDAC inhibitor PCI-24781 decreases RAD51 expression and inhibits homologous recombination, Proceedings of the National Academy of Sciences of the United States of America (PNAS), vol. 104, Issue 94, 2007, pp. 19482-19487, 6 pages.
Aebi, "Catalase in vitro", Methods in Enzymology, ScienceDirect, vol. 105, 1984, pp. 121-126, 6 pages.
Amin et al., "Saffron: a potential candidate for a novel anticancer drug against hepatocellular carcinoma", PubMed, Hepatology, vol. 54, Issue 03, 2011, pp. 857-867, 11 pages.
Amin et al., "Defective Autophagosome Formation in p53-Null Colorectal Cancer Reinforces Crocin-Induced Apoptosis", International Joural of Molecular Sciences, vol. 16, 2015, pp. 1544-1561, 18 pages.
Assimopoulou et al., "Radical scavenging activity of *Crocus sativus* L. extract and its bioactive constituents", PubMed, Phytother Res., vol. 19, 2005, pp. 997-1000, 4 pages.
Bathaie SZ & Mousavi SZ, "New Applications and Mechanisms of Action of Saffron and its Important Ingredients", PubMed, Critical reviews in food science and nutrition, vol. 50, 2010, pp. 761-786, 26 pages.
Biswas SK & Lewis CE, "NF-κB as a central regulator of macrophage function in tumors", Journal of Leukocyte Biology, vol. 88, 2010, pp. 877-884, 8 pages.
Bolden et al., "Anticancer activities of histone deacetylase inhibitors", PubMed, Nature reviews. Drug discovery, vol. 5, 2006, pp. 769-784, 16 pages.
Das et al., "Saffron suppresses oxidative stress in DMBA-induced skin carcinoma: A histopathological study", PubMed, Acta Histochemica, vol. 112, 2010, pp. 317-327, 11 pages.
Escribano et al., "Crocin, safranal and picrocrocin from saffron (*Crocus sativus* L) inhibit the growth of human cancer cells in vitro", Elsevier, Cancer Letters, vol. 100, 1996, pp. 23-30, 8 pages.
Espandiaria et al., "Comparison of different initiation protocols in the resistant hepatocyte model", Elsevier, Toxicology, vol. 206, 2005, pp. 373-381, 9 pages.
Ferlay et al., "Estimates of worldwide burden of cancer in 2008: GLOBOCAN 2008", International Journal of Cancer, UICC Global Cancer Control,. vol. 127, 2010, pp. 2893-2917, 26 pages.
Peterson, "A simplification of the protein assay method of Lowry et al. which is more generally applicable", Analytical Biochemistry, vol. 83, Issue 2, 1977, pp. 346-356, 11 pages.
Greenlee, "Natural products for cancer prevention", Seminars in Oncology Nursing, vol. 28, Issue 1, 2012, pp. 29-44, 16 pages.
Habig et al., "Glutathione S-transferases. The first enzymatic step in mercapturic acid formation", The Journal of Biological Chemistry, vol. 294, Issue 22, 1974, pp. 7130-7139, 11 pages.
Hariri et al., "The effect of crocin and safranal, constituents of saffron, against subacute effect of diazinon on hematological and genotoxicity indices in rats", Elsevier, ScienceDirect, Phytomedicine, vol. 18, Issue 6, 2011, pp. 499-504, 6 pages.
Hosseinzadeh & Sadeghnia, "Effect of safranal, a constituent of *Crocus sativus* (saffron), on methyl methanesulfonate (MMS)-induced DNA damage in mouse organs: an alkaline single-cell gel electrophoresis (comet) assay", DNA and Cell Biology, vol. 26, Issue 12, 2007, pp. 841-846, 6 pages.
Javadi & Emami, "A survey on saffron in major Islamic traditional medicinal books", ResearchGate, Iranian Journal of Basic Medical Science, vol. 16, Issue 1, 2013, pp. 1-11, 12 pages.
Karagiannis & El-Osta, "Chromatin modifications and DNA double-strand breaks: the current state of play", Nature Publishing Group, Leukemia, vol. 21, Issue 2, 2007, pp. 195-200, 6 pages.

(Continued)

*Primary Examiner* — James D. Anderson
(74) *Attorney, Agent, or Firm* — Hayes Soloway P.C.

(57) ABSTRACT

Methods of preventing the formation of liver cancer in a subject are described herein. In the disclosed methods, a prophylactically effective amount of safranal may be administered to a subject. In some embodiments, the subject may suffer from hepatic oxidative stress and/or hepatic inflammation. In another aspect, methods of preventing the formation of a liver cancer in a subject are disclosed that include monitoring the level of a liver cancer marker and administering a prophylactically effective amount of safranal to the subject, such that the effective amount is effective to maintain a normal level of the liver cancer marker.

11 Claims, 12 Drawing Sheets

(56) References Cited

PUBLICATIONS

Hillegass et al., "Assessment of myeloperoxidase activity in whole rat kidney", Journal of Pharmacological Methods, vol. 24, Issue 4. 1990, pp. 285-295, 11 pages.

Loria et al., "Myeloperoxidase: A New Biomarker of Inflammation in Ischemic Heart Disease and Acute Coronary Syndromes", Hindawi Publishing Corporation, Mediators of Inflammation, vol. 2008, Article ID 135625, 2008, 4 pages.

Luedde & Schwabe, "NF-κB in the liver-linking injury, fibrosis and hepatocellular carcinoma", R.F. National Rev. Gastroenterol Hepatol, vol. 8, 2011, pp. 108-118, 11 pages.

Sherman, "Hepatocellular carcinoma: epidemiology, surveillance, and diagnosis", Thieme Medical Publishers, Inc., Seminars in Liver Disease, vol. 30, Issue 1, 2010, pp. 3-16, 14 pages.

Marra et al., "Molecular targets and oxidative stress biomarkers in hepatocellular carcinoma: an overview", Journal of Translational Medicine, vol. 9, Issue 1, 2011, 14 pages.

Uchiyama & Mihara, "Determination of malonaldehyde precursor in tissues by thiobarbituric acid test", Academic Press, Inc., Analatical Biochemistry, vol. 86, Issue 1, 1978, pp. 271-278, 8 pages.

Minucci & Pelicci, "Histone deacetylase inhibitors and the promise of epigenetic (and more) treatments for cancer", —Nature Publishing Group, Nature Reviews on Cancer, vol. 6, Issue 1, 2006, pp. 38-51, 14 pages.

Morabito et al., "Lipid peroxidation and protein oxidation in patients affected by Hodgkin's lymphoma". Taylor&Francis healthsciences, Rapid Communication, Mediators of Inflammation, vol. 13, Issues 5/6, 2004, pp. 381-383, 4 pages.

Nahon et al., P, "Hepatic iron overload and risk of hepatocellular carcinoma in cirrhosis", Elsevier Masson, ScienceDirect, Gastroenterol Clinical Biololgy, vol. 34, Issue 1, 2010, pp. 1-7, 7 pages.

Nandi & Chatterjee, "Assay of superoxide dismutase activity in animal tissues", Journal Bioscience, vol. 13, Issue 3, 1988, pp. 305-315, 11 pages.

Park et al., "Diethylnitrosamine (DEN) induces irreversible hepatocellular carcinogenesis through overexpression of G1/S-phase regulatory proteins in rat", Elsevier, Toxicology Letters, vol. 191, 2009, pp. 321-326, 6 pages.

Pikarsky et al., "NF-kappaB functions as a tumour promoter in inflammation-associated cancer", Nature Publishing Group, vol. 431, 2004, pp. 461-466, 7 pages.

Reuter et al., "Oxidative stress, inflammation, and cancer: how are they linked?", National Institute of Health, NIH Public Access, Free Radic Biol Med., vol. 49, Issue 11, 2010, pp. 1603-1616, 40 pages.

Reznick & Packer, "Oxidative damage to proteins: spectrophotometric method for carbonyl assay", Academic Press, Inc., Methods in Enzymology, vol. 233, 1994, 357-363, 7 pages.

Rikimaru et al., "Clinical significance of histone deacetylase 1 expression in patients with hepatocellular carcinoma", Karger AG, Basel, Laboratory/Clinical Translation Research, Oncology, vol. 72, 2007, pp. 69-74, 6 pages.

Rios et al., "An update review of saffron and its active constituents", John Wiley & Sons, Ltd., ResearchGate, Phytotherapy Research. vol. 10, 1996, pp. 189-193, 6 pages.

Roberts et al., "Role of the Kupffer Cell in Mediating Hepatic Toxicity and Carcinogenesis", Toxicological Sciences, vol. 96, Issue 1, 2007, pp. 2-15, 15 pages.

Sakai & Muramatsu, "Regulation of GST-P Gene Expression During Hepatocarcinogenesis". Methods in Enzymology, vol. 401, 2005, pp. 42-61, 20 pages.

Sakai & Muramatsu, "Regulation of glutathione transferase P: a tumor marker of hepatocarcinogenesis", Elsevier, ScienceDirect, Biochemical and Biophysical Research Communications, vol. 375, 2007 pp. 575-578, 4 pages.

Scholzen & Gerdes, "The Ki-67 protein: from the known and the unknown", Wiley-Liss, Inc., Journal of Cellular Physiology, vol. 182, 2000, pp. 311-322, 12 pages.

Starley et al., "Nonalcoholic fatty liver disease and hepatocellular carcinoma: a weighty connection", Hepatology, vol. 51, Issue 5, 2010, pp. 1820-1832, 13 pages.

Surh et al., "Molecular mechanisms underlying chemopreventive activities of anti-inflammatory phytochemicals: down-regulation of COX-2 and iNOS through suppression of NF-kappa B activation", Elsevier, Mutation Research, =Fundamental and Molecular Mechanisms of Mutagenesis, vol. 480-481, 2001, pp. 243-268, 26 pages.

Tew et al., "The role of glutathione S-transferase P in signaling pathways and S-glutathionylation in cancer", Elsevier, ScienceDirect, Free Radical Biology & Medicine, vol. 51, 2011, pp. 299-313, 15 pages.

Ueno & Linder, "Detection of epithelial cell death in the body by cytokeratin 18 measurement", Elsevier, ScienceDirect, Biomedecine & Pharmacotherapy, vol. 59, 2005, pp. 359-362, 4 pages.

Valko et al., "Free radicals, metals and antioxidants in oxidative stress-induced cancer", Elsevier, ScienceDirect, Chemico-Biological Interactions, vol. 160, 2006, pp. 1-40, 40 pages.

Doorn et al., "Synergistic effects of phorone on the hepatotoxicity of bromobenzene and paracetamol in mice", Elsevier/North-Holland Scientifc Publishers Ltd., Toxicology, vol. 11, Issue 3, 1978, pp. 225-233, 9 pages.

Weichert, "HDAC expression and clinical prognosis in human malignancies", Elsevier, ScienceDirect, Cancer Letters, vol. 280, Issue 2, 2009, pp. 168-176, 9 pages.

Winterhalter & Straubinger, ,"Saffron—Renewed Interest in an Ancient Spice", Taylor & Francis, Food Reviews International, vol. 16, Issue 1, 2000, pp. 39-59, 23 pages.

Yang Xu, "Regulation of p53 responses by post-translational modifications", Nature Publishing Company, News and Commentary, Cell Death and Differentiation, vol. 10, 2003, pp. 400-403, 4 pages.

Yuan et al., "Histone deacetylase activity assay", Humana Press, Srikumar P. Chellappan (ed.), Chromatin Protocols: Second Edition, vol. 523, 2009, pp. 279-293, 15 pages.

Bachrach, "Contribution of selected medicinal plants for cancer prevention and therapy", Versita, Scientific Journal of the Faculty of Medicine, Acta Facultatis Medicae Naissensis, vol. 29, Issue 3, 2012, pp. 117-123, 7 pages.

Zhang et al., "Attenuated DNA damage repair by trichostatin A through BRCA1 suppression", BioOne, Radiation Research, vol. 168, Issue 1, 2007, pp. 115-124, 11 pages.

Ruhul Amin et al., "Evasion of anti-growth signaling: A key step in tumorigenesis and potential target for treatment and prophylaxis by natural compounds", Elsevier, ScienceDirect, Seminars in Cancer Biology, vol. 35, 2015, pp. S55-S77, 23 pages.

Yaswen et al., "Therapeutic targeting of replicative immortality", Elsevier, ScienceDirect, Seminars in Cancer Biology, vol. 35, 2015, pp. S104-S128, 25 pages.

Samadi et al., "A multi-targeted approach to suppress tumor-promoting inflammation", Elsevier, ScienceDirect, Seminars in Cancer Biology vol. 35, 2015, pp. S151-S184, 34 pages.

Block et al., "Designing a broad-spectrum integrative approach for cancer prevention and treatment", Elsevier, ScienceDirect, Seminars in cancer biology, vol. 35, 2015, pp. S276-S304, 29 pages.

Hamza et al., Melissa officinalis protects against doxorubicin-induced cardiotoxicity in rats and potentiates its anticancer activity on MCF-7 cells, PLoS ONE, Chapter 3, 2016, 25 pages.

Mah Al-Akhras et al., "Introducing Cichorium pumilum as a potential therapeutical agent against drug-induced benign breast tumor in rats", Informa Healthcare USA, Electromagnetic Biology and Medicine 31, Issue 4, 2012, pp. 299-309, 11 pages.

Amin et al., Neural network assessment of herbal protection against chemotherapeutic-induced reproductive toxicity, BioMed Central, Theoretical Biology and Medical Modelling, vol. 9, Issue 1, 2012, 1 page.

Amin, "Protective effect of green algae against 7, 12-dimethylbenzanthrancene (DMBA)-induced breast cancer in rats", Academic Journals Inc., International Journal of Cancer Research vol. 5, Issue 1, 2009, pp. 12-24, 14 pages.

Amin, A. et al., "Saffron-based crocin prevents early lesions of liver cancer: In vivo, In vitro and network Analyses", Recent Patents on Anti-Cancer Drug Discovery, vol. 11, 2016, pp. 121-133, 13 pages.

(56) References Cited

PUBLICATIONS

Amin et al., "Saffron: A potential candidate for a novel anticancer drug against hepatocellular carcinoma", Hepatobiliary Malignancies, Hepatology, vol. 54, 2011, pp. 857-867, 11 pages.
Al-Hrout et al., "Safranal induces DNA double-strand breakage and ERstress-mediated cell death in hepatocellular carcinoma cells", Scientific Reports, vol. 8, Issue 1, 2018, 15 pages.
Hamza et al., "Molecular characterization of the grape seeds extract's effect against chemically induced liver cancer: In vivo and in vitro analyses", Scientific Reports, vol. 8, 2018, 16 pages.
Bajbouj et al., "The anticancer effect of saffron in two p53 isogenic colorectal cancer cell lines", BioMed Central, Research Article, BMC Complementary & Alternative Medicine, vol. 12, 2012, pp. 1-9, 9 pages.
Amin & Buratovich, "The anti-cancer charm of flavonoids: a cup-of-tea will do!", Bentham Science Publishers Ltd., Recent patents on anti-cancer drug discovery, vol. 2, 2007, pp. 109-117, 10 pages.
Amin & Mousa, "Merits of anti-cancer plants from the Arabian Gulf region", Cancer Therapy, vol. 5, 2007, pp. 55-66, 13 pages.
Amin & Ghoneim, "Zizyphus spina-christi protects against carbon tetrachloride-induced liver fibrosis in rats", Elsevier, ScienceDirect, Food and Chemical Toxicology, vol. 47, 2009, pp. 2111-2119, 10 pages.
Amin et al., "Spirulina protects against cadmium-induced hepatotoxicity in rats", Science Publications, American Journal of Pharmacology and Toxicology, vol. 1, Issue 2, 2006, pp. 21-25, 6 pages.
Amin, "Chemopreventive effect of chlorella on the antioxidant system in 7, 12-Dimethylbenz [a] anthracene-induced oxidative stress in liver", Science alert, Asian Network for Scientific Information, International Journal of Pharmacology, vol. 4, Issue 3, 2008, pp. 169-176, 9 pages.
Amin et al., "Insights into glycan biosynthesis in chemically-induced hepatocellular carcinoma in rats: A glycomic analysis", Baishideng Publishing Group Inc., World J Gastroenterol, vol. 21, Issue 20, 2015, pp. 6167-6179, 14 pages.
Kamal et al., "Inhibitory properties of camel whey protein hydrolysates toward liver cancer cells, dipeptidyl peptidase-IV, and inflammation", Journal of Dairy Science Association, vol. 101, Issue 10, 2018, pp. 8711-8720, 10 pages.
Al-Dabbagh et al., "Salvadora persica (Miswak): antioxidant and Promising Antiangiogenic Insights", Scientific Research Publishing, American Journal of Plant Sciences vol. 9, Issue 06, 2018, pp. 1228-1244, 17 pages.
Al-Dabbagh et al., "Antioxidant and anticancer activities of chamomile (*Matricaria recutita* L.)", BMC research notes, vol. 12, Issue 3, 2019, 8 pages.
Al-Dabbagh et al., "Antioxidant and anticancer activities of Trigonella foenum-graecum, Cassia acutifolia and Rhazya stricta", Research Article, BMC complementary and alternative medicine, vol. 18:240, 2018, 12 pages.
Hamza et al., "Mechanistic insights into the augmented effect of bone marrow mesenchymal stem cells and thiazolidinediones in streptozotocin-nicotinamide induced diabetic rats", Scientific Reports, vol. 8, Issue 1, 2018, 18 pages.
Samarghandian & Boskabady, "Caspase-dependent pathway in apoptosis induced by Safranal in alveolar human lung cancer cell line", Research in Pharmaceutical Sciences, 2012, vol. 7, Issue 5, 1 page.
Samarghandian & Shabestari, "DNA fragmentation and apoptosis induced by safranal in human prostate cancer cell line", Indian Journal of Urology, 2013, vol. 29, Issue 3, pp. 177-183, 3 pages.
Amin & Lowe, "Plant-based anticancer drug development: advancements and hurdles", Journal of Gastrointestinal & Digestive System, 2012, vol. 2, Issue 5, 2 pages.
Al-Hrout et al., "Cancer and Biotechnology: A Matchup that Should Never Slowdown", Springer Int'l Publishing, Biotechnology and Production of Anti-Cancer Compounds, 2017, pp. 73-97, 25 pages.
Al-Akhras et al., "Sensitization of photohemolysis by a new extraction from flowers and aerial parts of Cichorium Pumilum Jacq: Effect of inulin and hydrogen peroxide", ResearchGate, American Journal of pharmacology and toxicology, 2007, vol. 2, Issue 2, pp. 75-79, 5 pages.

* cited by examiner

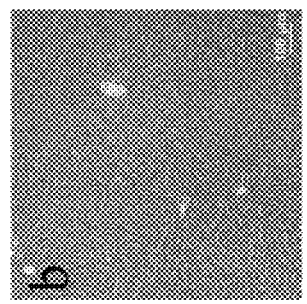
FIG. 2A3
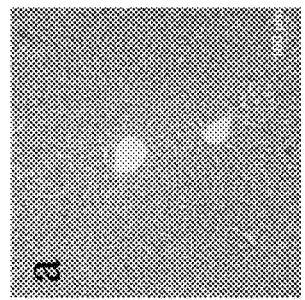
FIG. 2A2
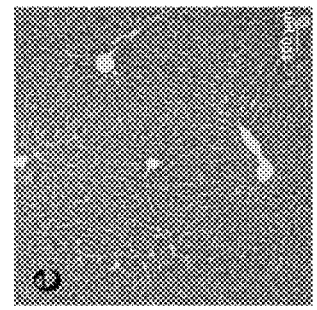
FIG. 2A5
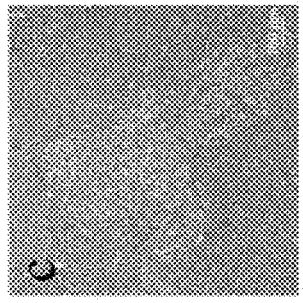
FIG. 2A1
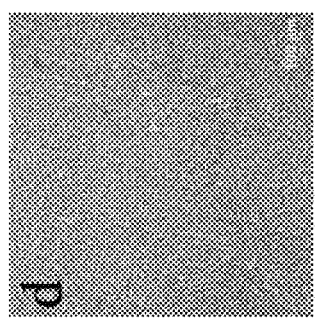
FIG. 2A4

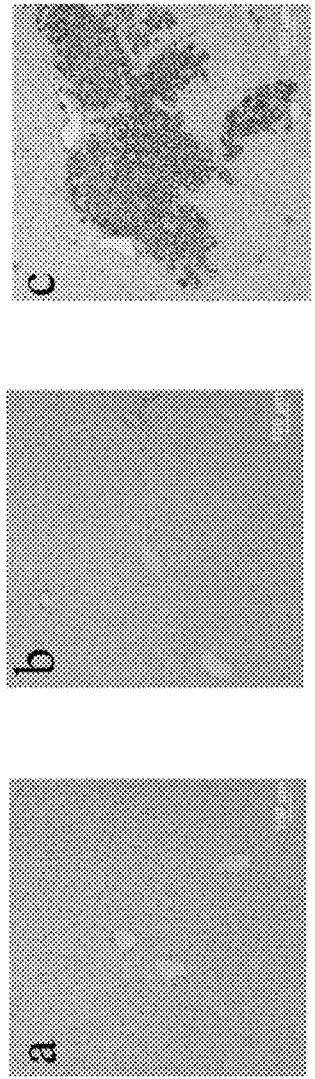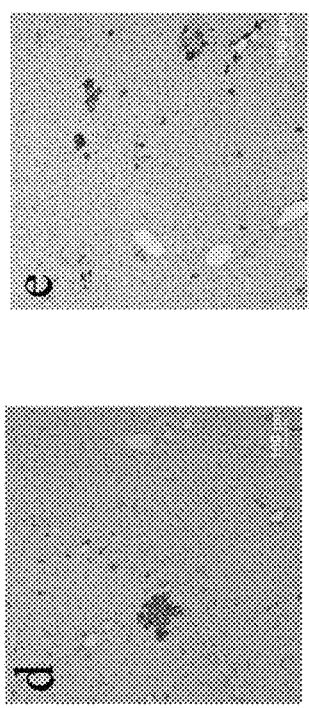

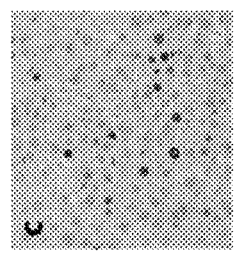
FIG. 3A1
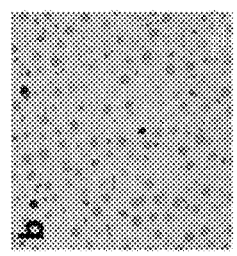
FIG. 3A2
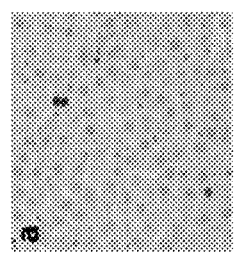
FIG. 3A3
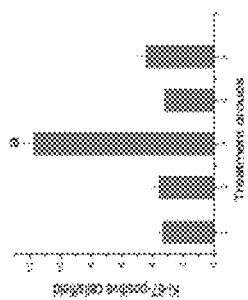
FIG. 3A4
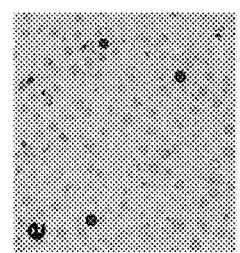
FIG. 3A5
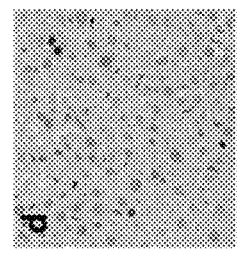
FIG. 3A6

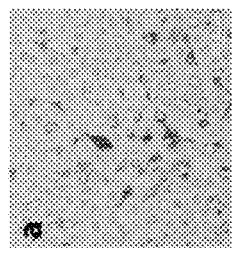
FIG. 3B3
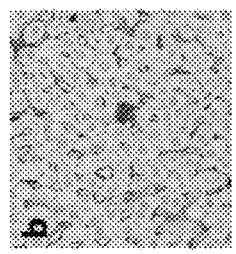
FIG. 3B2
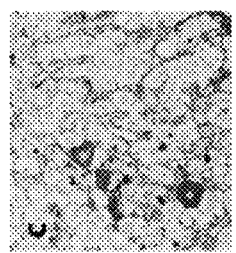
FIG. 3B1
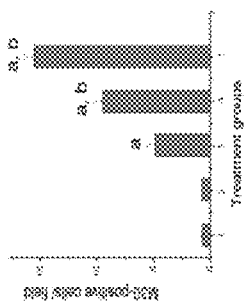
FIG. 3B6
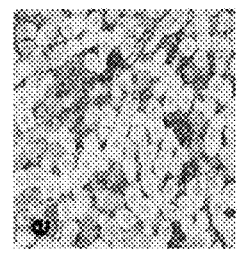
FIG. 3B5
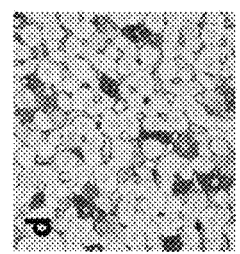
FIG. 3B4

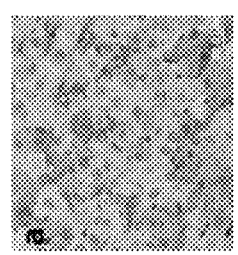
FIG. 3C1
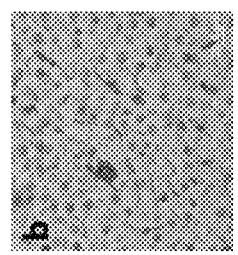
FIG. 3C2
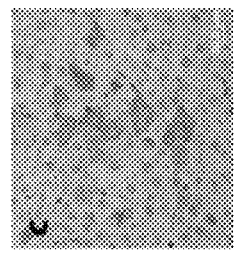
FIG. 3C3
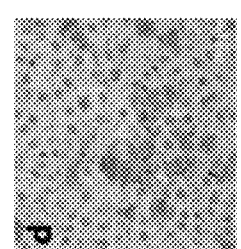
FIG. 3C4
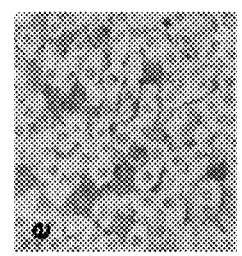
FIG. 3C5
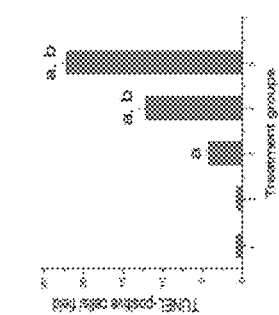
FIG. 3C6

| Species | Reference body weight (kg) | Working weight range (kg) | Body surface area (m²) | To convert dose in mg/kg to dose in mg/m², multiply by $K_m$ | To convert animal dose in mg/kg to HED in mg/kg, either Divide animal dose by | Multiply animal dose by |
|---|---|---|---|---|---|---|
| Human | 60 | — | 1.62 | 37 | — | — |
| Mouse | 0.02 | 0.011-0.034 | 0.007 | 3 | 12.3 | 0.081 |
| Hamster | 0.08 | 0.047-0.157 | 0.016 | 5 | 7.4 | 0.135 |
| Rat | 0.15 | 0.08-0.27 | 0.025 | 6 | 6.2 | 0.162 |
| Ferret | 0.30 | 0.16-0.54 | 0.043 | 7 | 5.3 | 0.189 |
| Guinea pig | 0.40 | 0.208-0.700 | 0.05 | 8 | 4.6 | 0.216 |
| Rabbit | 1.8 | 0.90-3.0 | 0.15 | 12 | 3.1 | 0.324 |
| Dog | 10 | 5-17 | 0.50 | 20 | 1.8 | 0.541 |
| Monkeys (rhesus) | 3 | 1.4-4.9 | 0.25 | 12 | 3.1 | 0.324 |
| Marmoset | 0.35 | 0.14-0.72 | 0.06 | 6 | 6.2 | 0.162 |
| Squirrel monkey | 0.60 | 0.29-0.97 | 0.09 | 7 | 5.3 | 0.189 |
| Baboon | 12 | 7-23 | 0.60 | 20 | 1.8 | 0.541 |
| Micro pig | 20 | 10-33 | 0.74 | 27 | 1.4 | 0.730 |
| Mini pig | 40 | 25-64 | 1.14 | 35 | 1.1 | 0.946 |

FIG. 6

PREVENTION OF LIVER CANCER WITH SAFRANAL-BASED FORMULATIONS

TECHNICAL FIELD

The present invention relates to prophylactic formulations and methods for preventing liver cancer by administering safranal to a subject.

BACKGROUND

Each year, more people are diagnosed with hepatocellular carcinoma (HCC); the most common type of primary liver cancer, the sixth common cancer, and the second leading cause of death by cancer worldwide; according to WHO. Multiple factors increase the risk of developing HCC; for instance, chronic hepatitis (B and C) infection account for 70%-90% of HCC cases by presenting a permissive environment for HCC development. Other HCC risk factors include alcoholism, non-alcohol fatty liver disease, iron overload, and exposure to carcinogenic agents, for example chemical agents, pharmaceutical agents having carcinogenic side effects, or forms of radiation causing cancer. Diethylnitrosamine (DEN), for example, is considered a chemical carcinogenic agent that we may be exposed to on day-to-day basis. DEN is a component in processed food, cosmetics, gasoline, and tobacco smoke; and it is used to study different types of benign and malignant tumors in humans by inducing resembling lesions in rats. Early stages of HCC show no symptoms, and most patients are diagnosed at advanced stages; hence, the prognosis of HCC remains unsatisfactory. In addition, HCC exhibits a high rate of recurrence after resection or ablation; and is considerably resistant to cytotoxic chemotherapy, with a very limited number of available treatments. Thus, alternative therapeutics has been considered; one of which is preventive control to protect against cancer.

Considering their great efficacy and low toxicity, natural herbs and plants have been extensively studied and proposed as a chemoprotective therapy for many diseases including cancer. A number of medicinal plants have been suggested for cancer prevention and therapy for several reasons; they contain nutritional and anti-tumor compounds, are able to delay or prevent cancer onset, can boost the physiological status and the immune system, and most importantly, they represent a great alternative to conventional cancer treatments by decreasing or even preventing their side effects. Hence, antioxidative, anti-inflammatory, and hepatoprotective properties possessed by some natural compounds qualify them as potential candidates to protect against tumor initiation and growth.

There has been a considerable interest in a particular plant product, saffron. It comes from *Crocus sativus* flower, particularly, the dried stigmas of its flower. It has been used since ancient times in Egypt and Rome as a remedy and a culinary spice. In folk medicine, saffron has been used as antidepressant, antispasmodic, respiratory decongestant and as remedies against scarlet fever, asthma, and smallpox. Many investigations have demonstrated the biological effects of saffron and its active constituents in vivo and in vitro. Saffron and its active constituents exhibited antioxidant, anti-inflammation, antitumor activities.

Upon chemical analysis, more than 160 components were detected in saffron stigmas, including safranal, crocin, and picrocrocin, which attributes the saffron aroma, color, and bitter taste, respectively. These saffron active biomolecules, safranal, crocin, and picrocrocin were reported to inhibit the growth of HeLa cells. For instance, safranal is known to exert potent anti-inflammatory, antioxidant and anti-cancer properties and was found to induce apoptosis in both alveolar human lung cancer A549, and human prostate cancer PC-3 cell lines. Safranal is known by the IUPAC name 2,6,6-trimethylcyclohexa-1,3-diene-1-carbaldehyde. Its molecular formula is $C_{10}H_{14}O$, its molecular weight is 150.221 g/mol, and its density at 25° C. is 973 mg/ml. Its structural formula is:

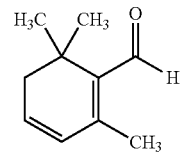

In previous publication, saffron extract was proposed as a promising candidate for cancer chemoprevention. However, given the sheer number of biomolecules present in the extract, and the relative low amounts of safranal contained therein, the effects of safranal alone on tumorigenesis is yet to be determined.

When promoting carcinogenesis experimentally, foci of altered hepatocytes serve as pre-neoplastic indicators of HCC, weeks or months prior to its emergence; which resembles the progression of human hepatocarcinogenesis. For safranal to be introduced as a potential chemopreventive drug against liver cancer, it would be advantageous to develop an appropriate animal model where dietary intake of safranal can be assessed.

SUMMARY OF THE EMBODIMENTS

In a first aspect of the present invention, there is provided a method of preventing the formation of liver cancer in a subject. The method includes administering a prophylactically effective amount of safranal to the subject. The subject may suffer from either or both of hepatic oxidative stress and hepatic inflammation. In example embodiments, the amount of safranal may be from about 15 mg/day to 60 mg/day per kg body weight of the subject, from about 20 mg/day to about 50 mg/day per kg body weight of the subject, or about 25 mg/day to about 45 mg/day per kg body weight of the subject.

In a second aspect of the present invention, there is provided a method of preventing the formation of a liver cancer in a subject. The method includes monitoring the level of a liver cancer marker, and administering a prophylactically effective amount of safranal to the subject, where said effective amount is effective to maintain a normal level of the liver cancer marker. In one embodiment, the subject suffers from a liver condition conducive to liver cancer. The liver condition may be selected from the group consisting hepatitis B, hepatitis C, cirrhosis, non-alcohol fatty liver disease, iron overload, and exposure to environmental carcinogens. The liver cancer marker may be an oxidative stress marker. Example oxidative stress markers include malondialdehyde (MDA), catalase (CAT), superoxide dismutase (SOD), myeloperoxidase (MPO), serum protein carbonyl (P.carbonyl), and combinations thereof. The liver cancer marker may be an inflammation marker. Example inflammation markers include tumor necrosis factor alpha (TNF-α), cyclooxygenase-2 (COX-2), and i-nitrous oxide synthase (iNOS). In example embodiments, the amount of safranal may be from about 15 mg/day to 60 mg/day per kg body weight of the subject, from about 20 mg/day to about 50 mg/day per kg body weight of the subject, or about 25 mg/day to about 45 mg/day per kg body weight of the subject.

In a third aspect of the present invention, there is provided a method of preventing the formation of a liver cancer in a subject, the cancer resulting from exposure to a carcinogenic agent. The method includes administering to the subject a prophylactically effective amount of safranal. In exemplary embodiments, the carcinogenic agent is selected from the group consisting of a chemical agent, a pharmaceutical agent, a form of radiation, and combinations thereof. In example embodiments, the amount of safranal may be from about 15 mg/day to 60 mg/day per kg body weight of the subject, from about 20 mg/day to about 50 mg/day per kg body weight of the subject, or about 25 mg/day to about 45 mg/day per kg body weight of the subject.

BRIEF DESCRIPTION OF THE FIGURES

The invention can be better understood with reference to the following figures and description. The components in the figures are not necessarily to scale and are not intended to accurately represent molecules, cells, cell organelles, tissues, or their interactions, emphasis instead being placed upon illustrating the principles of the invention.

FIGS. 2A1-2A5 show that safranal inhibits DEN-induced increase of foci of altered hepatocytes (FAH) and induction of GST-p expression in liver:

FIG. 2A. H & E panel: Representative Images of hematoxylin and eosin-stained section in the livers of all groups studied. Control (FIG. 2A1); High dose of safranal alone (FIG. 2A2); Induced-cancer group (FIG. 2A3); Induced-cancer+Low dose safranal (FIG. 2A4); Induced-cancer+High dose safranal (FIG. 2A5); FAH was observed in liver sections from DEN-treated group, (Scale bar=100 μm).

FIGS. 2B1-2B5 illustrate a GST-p panel: Representative Images of immunohistochemical GST-p-stained section in the livers of all groups studied. Control (FIG. 2B1); High dose of safranal alone (FIG. 2B2); Induced-cancer group (FIG. 2B3); Induced-cancer+Low dose safranal (FIG. 2B4); Induced-cancer+High dose safranal (FIG. 2B5), (Scale bar=100 μm).

FIGS. 3A1-3A6, 3B1-B6, and 3C1-C6 illustrate the effects of safranal on cell proliferation and apoptosis:

FIGS. 3A1-3A6 (Ki-67 panel): Representative images of immunohistochemical staining with Ki-67 in the liver section from all the groups are shown. Control (FIG. 3A1); High dose of safranal alone (FIG. 3A2); Induced-cancer group (FIG. 3A3); Induced-cancer+Low dose safranal (FIG. 3A4); Induced-cancer+High dose safranal (FIG. 3A5), (Scale bar=20 μm). (FIG. 3A6) Quantitative analysis of Ki-67-positive cells in different experimental groups. The positive expression of Ki-67 in each section was calculated by counting the number of brown staining in ten fields at 400× magnifications then the number of positive cells/field. Values expressed as mean±SEM for eight animals in each group. Significance was determined by one-way analysis of variance followed by Dennett's t test: $^{a}$P<0.001 vs. normal group; $^{b}$P<0.001vs. DEN group.

FIGS. 3B1-3B6 (M30 panel): Representative images of immunohistochemical staining with M30 in the liver section from all the groups are shown. Control (FIG. 3B1); High dose of safranal alone (FIG. 3B2); Induced-cancer group (FIG. 3B3); Induced-cancer+Low dose safranal (FIG. 3B4); Induced-cancer+High dose safranal (FIG. 3B5), (Scale bar=20 μm). (FIG. 3B6) Quantitative analysis of M30-positive cells in different experimental groups. The positive expression of M30 in each section was calculated by counting the number of brown staining in ten fields at 400× magnifications then the number of positive cells/field. Values expressed as mean±SEM for eight animals in each group. Significance was determined by one-way analysis of variance followed by Dennett's t test: $^{a}$P<0.001 vs. normal group; $^{b}$P<0.001vs. DEN group.

FIGS. 3C1-3C6 (TUNEL panel): Representative images of immunohistochemical staining with TUNEL in the liver section from all the groups are shown. Control (FIG. 3C1); High dose of safranal alone (FIG. 3C2); Induced-cancer group (FIG. 3C3); Induced-cancer+Low dose safranal (FIG. 3C4); Induced-cancer+High dose safranal (FIG. 3C5), (Scale bar=20 μm). (FIG. 3C6) Quantitative analysis of TUNEL-positive cells in different experimental groups. The positive expression of TUNEL in each section was calculated by counting the number of brown staining in ten fields at 400× magnifications then the number of positive cells/field. Values expressed as mean±SEM for eight animals in each group. Significance was determined by one-way analysis of variance followed by Dennett's t test: $^{a}$P<0.001 vs. normal group; $^{b}$P<0.001vs. DEN group.

(FIG. 4A) Representative images of immunohistochemical staining with p-TNF-R1 in the liver section from all the groups are shown. From left to right: Control, High dose of safranal alone, Induced-cancer group, Induced-cancer+Low dose safranal, Induced-cancer+High dose safranal, (Scale bar=20 μm). On each image a quantitative analysis of p-TNF-R1-positive cells is represented. The positive expression of p-TNF-R1 in each section was calculated by counting the number of brown staining in ten fields at 400× magnifications then the number of positive cells/field. Values expressed as mean±SEM for eight animals in each group. Significance was determined by one-way analysis of variance followed by Dennett's t test: $^{a}$P<0.001 vs. normal group; $^{b}$P<0.001vs. DEN group.

(FIG. 4B) Representative images of immunohistochemical staining with NF-kB-p65-stained section in the livers of all groups studied are shown. From left to right: Control, High dose of safranal alone, Induced-cancer group, Induced-cancer+Low dose safranal, Induced-cancer+High dose safranal, (Scale bar=20 μm). On each image a quantitative analysis of NF-kB-p65-positive cells is represented. The positive expression of NF-kB-p65 in each section was calculated by counting the number of brown staining in ten fields at 400× magnifications then the number of positive cells/field. Values expressed as mean±SEM for eight animals in each group. Significance was determined by one-way analysis of variance followed by Dennett's t test: $^{a}$P<0.001, $^{c}$P<0.01 vs. normal group 1; $^{b}$P<0.001, $^{d}$P<0.01 vs. DEN group.

(FIG. 4C) Effects of safranal on the TNF-α content in serum. Values are expressed as mean±SEM; n=8. $^{a}$P<0.001, $^{c}$P<0.01 vs. normal group 1; $^{b}$P<0.001, $^{d}$P<0.01 vs. DEN group. (FIG. 4D) Quantitative analysis of NF-kB-p65 nuclear localization represented as fold change (relative to control group). (FIG. 4E) Safranal inhibits HDAC activity. Values are expressed as mean±SEM; n=8.

(FIG. 5A) Viability of HepG2 cells after safranal treatment for 24 hrs. HepG2 cells were treated with 1 mM, 0.3 mM, 0.1 mM, 0.03 mM, 0.01 mM of safranal.

(FIG. 5B) Caspase-3/7 activities after safranal treatment for 48 hrs. HepG2 cells were treated with 1 mM, 0.7 mM, 0.5 mM of safranal.

(FIG. 5C) IL-8 secretion after safranal treatment. HepG2 cells were treated with 2 mM for 6 and 12 hrs, and subsequently, the supernatants were analyzed by IL-8 ELISA.

(FIG. 5D) Protein levels of p-Ikb and H2AX, after safranal treatment.

FIG. 6 is a table reporting human equivalent dose (HED) dosage factors based on body surface area of other species according to data obtained from the United States Food and Drug Administration draft guidelines.

DETAILED DESCRIPTION

Figure 1:
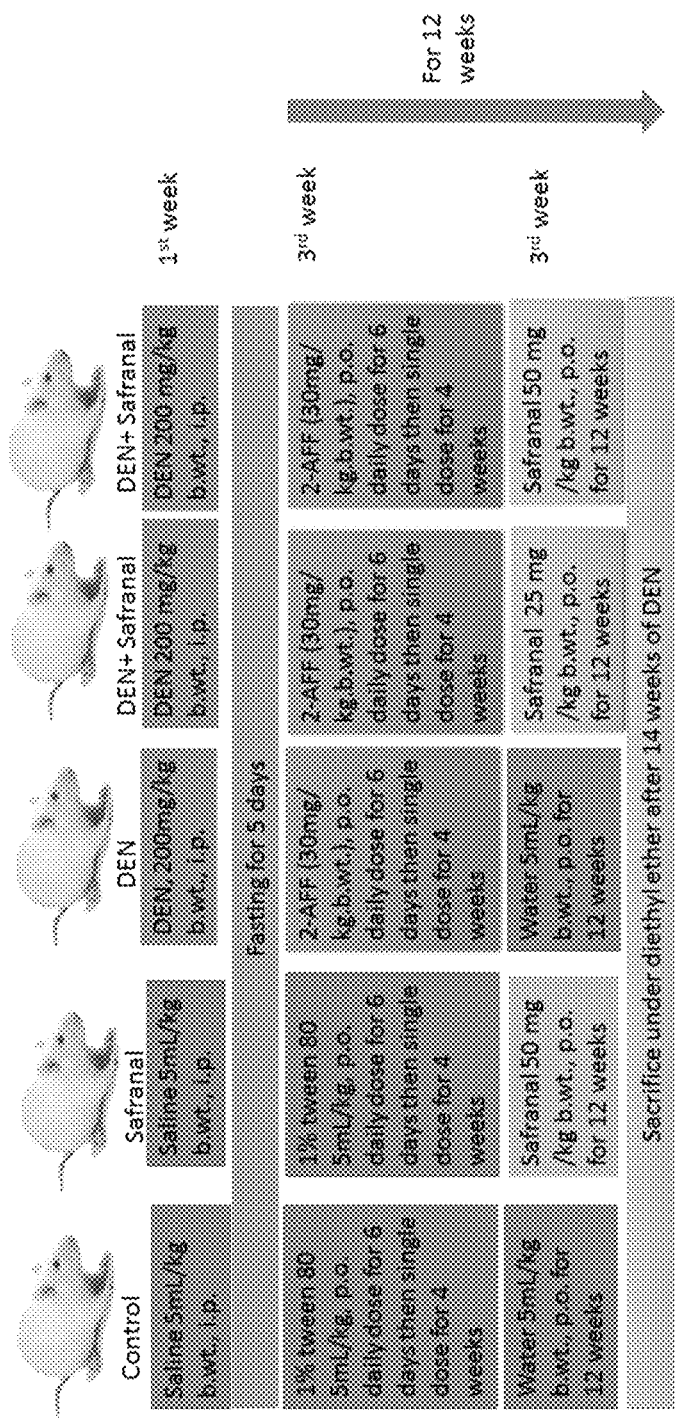
FIG. 1 illustrates the experimental design of a hepatocarcinogenesis model for evaluating the chemopreventive action of safranal against liver cancer.

The present invention is based on findings that prove that pre-treatment with safranal exerts liver cancer chemoprevention activity by acting against early hepatic preneoplastic events. In the study reported below, an initiation-promotion model was developed to imitate the latent period of human carcinogenesis early events. Carcinogenesis was initiated by injecting animals with a single dose of diethylnitrosamine (DEN), a carcinogen that has been used to induce lesions that resemble human benign and malignant tumors by causing DNA ethylation and mutagenesis. The initiation stage was followed by fasting and re-feeding, which serve as a growth stimulus; during which 2-acetyl aminofluorene (2-AAF) promoting agent was introduced to animals, to selectively induce proliferation of the initiated cell population in targeted tissue. Key regulators of different pathways were then assessed. Human hepatoma cell line "HepG2" cells were also used in vitro to assess safranal's effects in human liver cancer cells.

The findings from the study clearly showed the great efficacy of safranal pre-treatment in the prevention of HCC in DEN-treated rats. Safranal pre-treatment was efficient in inhibiting FAH formation in DEN-induced HCC models, restoring the antioxidant normal levels and reducing all tested oxidative stress markers. In addition, significant decreases in the activity of inflammatory markers, COX-2, iNOS, NF-kB, TNF-α and its receptor p-TNF-R1 were observed in DEN-induced HCC model pre-treated with safranal. Moreover, pre-treatment with safranal induced a reduction in the number of Kupffer cells and macrophages. These findings were also confirmed by the in vitro experiments on HepG2 cells.

In view of the foregoing findings, provided herein is a method of preventing the process of cancer formation of cancer in the liver prior to its occurrence. Safranal can prevent or reverse oncogenesis on a cellular level after the process is initiated, but prior to the formation of a detectable cancerous mass.

Safranal Compositions

A prophylactically effective amount of safranal or its pharmaceutically effective derivatives may be administered either alone or formulated together with one or more pharmaceutically acceptable carrier(s), diluent(s), or excipient (s). The carrier(s), diluent(s) or excipient(s) must be acceptable in the sense of being compatible with the other ingredients of the formulation, capable of pharmaceutical formulation, and not deleterious to the recipient thereof.

As illustrated above, safranal includes an α-β unsaturated aldehyde group and is therefore capable of forming hemiacetals, acetals, thioketals, silyl ethers, and other derivatives resulting from nucleophilic addition reactions to the β-carbon of the unsaturation. In instances where the safranal derivatives are pharmaceutically acceptable and easily cleavable under physiological conditions, one or more derivative may be administered to the patient as a pro-drug of safranal itself. The term "pharmaceutically acceptable safranal derivative", in this respect, refers to the pharmaceutically acceptable and easily cleavable groups of safranal, including hemiacetals, acetals, thioketals, silyl ethers, and nucleophilic addition products. These pro-drugs can be prepared in situ in the administration vehicle or in the dosage form manufacturing process, or by separately reacting safranal with a suitable reactant, and isolating the derivative thus formed during subsequent purification. Other derivatives that may serve as pro-drugs include pharmaceutically acceptable salts and hydrates. Therapeutically effective tautomers and isomers of safranal are also contemplated. Unless otherwise specified, the terms "composition of safranal", "composition including safranal", and "formulation of safranal" as used herein are intended to cover compositions and formulations including safranal itself and/or its pro-drugs such as: hemiacetals and acetals, pharmaceutically acceptable tautomers and isomers, and pharmaceutically acceptable salts thereof.

The composition may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of safranal include those suitable for oral, nasal, topical (including buccal and sublingual), rectal, vaginal and/or parenteral administration. The formulations may conveniently be presented in unit dosage form and may be prepared by any methods well known in the art of pharmacy. The amount of safranal which can be combined with a carrier material to produce a single dosage form will vary depending upon the host being treated, the particular mode of administration. The amount of an active ingredient which can be combined with a carrier material to produce a single dosage form will usually be that amount of the compound which produces a prophylactic effect. Usually, out of one hundred percent, this amount will range from about 1 wt % to about 99 wt % of active ingredient, preferably from about 5 wt % to about 70 wt %, most preferably from about 10 wt % to about 30 wt %.

In certain embodiments, a formulation of safranal includes an excipient selected from the group consisting of cyclodextrins, liposomes, micelle forming agents, e.g., bile acids, and polymeric carriers, e.g., polyesters and polyanhydrides; and an active ingredient that may be safranal and/or one of its pharmaceutically acceptable derivatives. In certain embodiments, an aforementioned formulation renders orally bioavailable safranal or its derivative.

Methods of preparing these formulations or compositions include the step of bringing into association safranal with the carrier and, optionally, one or more accessory ingredients. Usually, the formulations are prepared by uniformly and intimately bringing into association a compound of the present invention with liquid carriers, or finely divided solid carriers, or both, and then, if necessary, shaping the product.

Liquid dosage forms for oral administration of safranal include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A formulation of safranal may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also include buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

The tablets, and other solid dosage forms of the pharmaceutical of safranal or its pro-drugs, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations of the pharmaceutical compositions of safranal for rectal or vaginal administration may be presented as a suppository, which may be prepared by mixing safranal with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Dosage forms for the topical or transdermal administration of safranal include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required. The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to active compounds, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of safranal or its pro-drugs to the body. Such dosage forms can be made by dissolving or dispersing a compound in the proper medium. Absorption enhancers can also be used to increase the flux of the compound across the skin. The rate of such flux can be controlled by either providing a rate controlling membrane or dispersing the compound in a polymer matrix or gel.

Pharmaceutical compositions suitable for parenteral administration include one or more of safranal or its pro-drugs in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When safranal is administered as a pharmaceutical composition, to humans and animals, it can be given per se or as a pharmaceutical composition containing, for example, 0.1 to 99.5% (more preferably, 0.5 to 90%) of active ingredient in combination with a pharmaceutically acceptable carrier.

The preparations may be given orally, parenterally, topically, or rectally. They are of course given in forms suitable for each administration route. For example, they are administered in tablets or capsule form, by injection, inhalation, eye lotion, ointment, or suppository; administration by injection, infusion or inhalation; topical by lotion or ointment; and rectal by suppositories. Oral administrations are preferred.

Safranal may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, safranal may be formulated into pharmaceutically-acceptable dosage forms by conventional methods known to those of skill in the art. Safranal may be formulated for administration in any convenient way for use in human or veterinary medicine, by analogy with other pharmaceuticals.

Methods of Liver Cancer Prevention

The above safranal compositions may be used in novel prophylactic methods of liver cancer prevention. The methods include administering to an individual a prophylactically effective amount of a subject safranal composition. Administration of safranal according to embodiments of the present invention has shown to both lower and maintain liver tumor markers at a normal level, thereby indicating its usefulness in preventing the formation of liver cancer. A prophylactically effective amount of safranal is that amount which provides a decrease in the level of a marker to a normal level and which maintains the marker at the normal level.

In an exemplary embodiment, safranal is administered to a subject following the detection of a condition or in the presence of a factor known to increase the risk of developing liver cancer. Liver conditions known to induce carcinogenesis include viral diseases such as hepatitis B and hepatitis C, liver cirrhosis from excessive alcohol consumption, genetic factors, and exposure to carcinogenic agents. Common carcinogenic agents include carcinogenic chemicals, pharmaceuticals known to have carcinogenic side effects, and forms of radiation causing cancer.

In a further embodiment, liver cancer is prevented by administering safranal when elevated levels of one or more markers associated with liver tumorigenesis are measured in the subject. Oxidative stress markers diagnostic of compromised antioxidant status in the liver include abnormal levels of malondialdehyde (MDA), catalase (CAT), superoxide dismutase (SOD), myeloperoxidase (MPO), and serum protein carbonyl (P.carbonyl). Histological examination can reveal foci of altered hepatocytes (FAH) representing preneoplastic lesions, as shown in various models of hepatocarcinogenesis. Placental glutathione s-transferase (GST-p) is another reliable liver tumor-biomarker that is expressed throughout hepatocarcinogenesis. Overexpression of Ki-67 has also been found to be consistent with tumorigenesis. A permissive environment for cancer development is also characterized by increases in the expression levels of inflammation markers, for example tumor necrosis factor alpha (TNF-α), cyclooxygenase-2 (COX-2), and i-nitrous oxide synthase (iNOS).

Administration of safranal according to the present invention has shown to both lower and maintain tumor markers at normal levels, thereby indicating its usefulness in preventing the formation of liver cancer. The use of safranal in the prevention of a malignant liver tumor in an embodiment of the present invention contemplates the daily administration of an effective amount of safranal orally. Other administration regimens, for example multiple daily dosages, are also contemplated depending on the needs of each individual subject. An effective amount of safranal is that amount which provides a decrease in the level of one or more of the above markers to a normal level and which maintains the marker(s) at the normal level.

Administration of Chemopreventive Compositions

Safranal or its pharmaceutically acceptable derivatives may be administered by any appropriate route. It will be appreciated that the preferred route may vary with, for example, the condition of the recipient of the safranal and the disease to be treated. In certain embodiments, the method includes orally administering an effective amount of a subject pharmaceutical composition to a subject. In some embodiments, the method includes parenterally administering an effective amount of a subject pharmaceutical composition to a subject.

The desired concentration of safranal in the composition will depend on absorption, inactivation, and excretion rates of the safranal as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Alternatively, the dosage of safranal may be determined by reference to its concentration in the plasma. For example, the maximum plasma concentration ($C_{max}$) and the area under the plasma concentration-time curve from time 0 to infinity (AUC (0-4)) may be used. Dosages for the present invention include those that produce the above values for $C_{max}$ and AUC (0-4) and other dosages resulting in larger or smaller values for those parameters.

Actual dosage levels of the active ingredients in the pharmaceutical compositions of this aspect of the invention may be varied so as to obtain an amount of safranal which is effective to achieve the desired prophylactic response for a particular subject, composition, and mode of administration, without being toxic to the subject.

The selected dosage level will depend upon a variety of factors including the activity of the safranal (or its pharmaceutically acceptable derivatives), the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the safranal composition required. For example, the physician or veterinarian could start doses of the compounds of the invention employed in the safranal composition at levels lower than that required in order to achieve the desired prophylactic effect and gradually increase the dosage until the desired effect is achieved.

Usually, a suitable daily dose of safranal that is contained in the prophylactic amount of the composition will be that amount of safranal which is the lowest dose effective to produce a prophylactic effect. Such an effective dose will usually depend upon the factors described above. If desired, the effective daily dose of safranal may be administered as two, three, four, five, six or more sub-doses administered separately at appropriate intervals throughout the day, optionally, in unit dosage forms. The precise time of administration and amount of any particular compound that will yield the most effective prophylactic treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

Exemplary doses of safranal fall in the range from about 0.001, 0.01, 0.1, 0.5, 1, 10, 15, 20, 25, 50, 100, 200, 300, 400, 500, 600, or 750 to about 1000 mg/day per kg body weight of the subject. In certain embodiments, the dose of safranal will typically be in the range of about 100 mg/day to about 1000 mg/day per kg body weight of the subject, specifically in the range of about 200 mg/day to about 750 mg/day per kg, and more specifically in the range of about 250 mg/day to about 500 mg/day per kg. In an embodiment, the dose is in the range of about 50 mg/day to about 250 mg/day per kg. In a further embodiment, the dose in the range of about 100 mg/day to about 200 mg/day per kg. In an embodiment, the dose is in the range of about 15 mg/day to 60 mg/day per kg. In a further embodiment, the dose is in the range of about 20 mg/day to 50 mg/day per kg. In an additional embodiment, the dose is in the range of about 25 mg/day to 45 mg/day per kg.

The data obtained from the cell culture assays and animal studies may be used in formulating a range of dosage for use in humans. For example, effective dosages achieved in one animal species may be extrapolated for use in another animal, including humans, as illustrated in the conversion table of FIG. 6 where human equivalent dose (HED) dosage factors based on body surface area of other species are reported. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

Kits

The present invention provides kits for preventing liver cancer. For example, a kit may include one or more pharmaceutical compositions of safranal as described above. The compositions may be pharmaceutical compositions comprising a pharmaceutically acceptable excipient. In still other embodiments, the invention provides a kits comprising one more pharmaceutical compositions and one or more devices for accomplishing administration of such compositions.

Materials and Methods

Materials

DEN, 2-AAF, 5, 5'-dithiobis-(2-nitrobenzoic acid thiobarbituric acid, Folin's reagent, pyrogallol, SOD enzyme, H2O2, and bovine albumin were obtained from Sigma Chemical Co. (St. Louis, Mo.). Nf-kB nuclear localization assay kit was purchased from (Ser. No. 10/007,889, Cayman Chemical Company, Ann Arbor, Mich., USA).

Primary antibodies of Ki-67, COX-2 (Clone SP 21), iNOS (Ab-1), and NF-kB-P65 (Rel A, Ab-1) were purchased from Thermo Fisher Scientific, Anatomical Pathology, Fremont, USA (1:100 dilutions). GST-p form was obtained from Medical and Biological Laboratories Co., Tokyo, Japan (1:1000 dilution). M30 CytoDeath was purchased from Enzo life Science, USA. ED-2 (1:300 dilution) and the phosphorylated form of tumor necrosis factor alpha receptor 1 (p-TNFR) were obtained from Santa Cruz, Calif., USA (1:200 dilution). Safranal (W338907 ALDRICH) was obtained from SIGMA-ALDRICH, USA. Administration of safranal (25 and 50 mg/kg. body wt) was intragastric.

Animals

All animal experiments were performed according to the guidelines of the Animal Research Ethics Committee, UAE University. Adult male albino Wistar rats (150 g to 200 g in weight) were provided with free access to standard pellet diet and tap water ad libitum, and were kept in polycarbonate cages lined with wood chip bedding, at room temperature (22° C.-24° C.) with a light/dark cycle of 12 hours. Prior to the experimental procedure, rats were adjusted to the environment for two weeks. All rats were acquired from UAE University Animal House, UAE.

Hepatocarcinogenesis Model

The experimental hepatocarcinogenesis model was developed according to a protocol by Espandiaria et al. that was adapted for our purposes. To initiate and promote hepatocarcinogenesis, diethylnitrosamine (DEN) and 2-acetylaminofluorene (2-AAF) were used, respectively. For hepatocarcinogenesis initiation in this model, a single DEN dose (200 mg/kg b.wt.) dissolved in saline was injected intraperitoneally. After initiation, all rats underwent one period of 5-days fasting, as mitotic proliferative stimuli. To promote hepatocarcinogenesis, 2-acetylaminofluorene (2-AAF) was introduced in the form of six daily intragastric doses (30 mg/kg in 1% Tween 80); two weeks after DEN treatment.

Experimental Design

Safranal at doses of 25 mg/kg by weight (b.wt.) and 50 mg/kg b.wt, was administrated orally to rats. These doses have been reported to suppress chemically-induced oxidative damage in rats. A total of 40 adult male albino Wistar rats were randomly divided into 8 groups (n=8) and were subjected to different treatments. Group 1 (control) was orally administered distilled water (5 ml/kg b.wt.) throughout the experimental duration and were injected with a single dose of saline. Group 2 (Safranal only) was subjected to a safranal dose (50 mg/kg b.wt.) through oral administration for the duration of the experimental period. Hepatocarcinogenesis was induced by DEN and promoted by 2-AAF, as reported previously, in group 3 (HCC). Rats in protective groups (groups 4-5) were treated with low/high doses of saffron-based safranal suspensions, at the beginning of promotion periods and continued for 12 weeks. The low dosage treatment with safranal consisted of 25 mg/kg b.wt., and the high dosage treatment consisted of 50 mg/kg b.wt. The experimental design is illustrated in FIG. 1.

Blood Samples

After 14 weeks of DEN administration, all animals were anesthetized by diethylether 24 hours post last treatment. Blood samples were collected via retro orbital puncture, and the animals were sacrificed.

Morphology and Histopathology

Diethylether-anesthetized rats were sacrificed and random samples of right, left, caudate lobes were excised and immediately fixed in 10% buffered formalin for the purpose of histological examination. Fixed tissue samples were processed and embedded in paraffin, and sectioned into five-micrometer sections. Cut sections were placed onto glass slides and routine staining by Hematoxylin and Eosin was performed prior to examination under light microscope (Olympus DP71). Liquid nitrogen was used to flash-freeze the remaining liver samples. Frozen samples were stored at −80° C.

Sample Preparation

To obtain serum, collected blood samples were centrifuged at 3000 rpm for 20 minutes (4° C.). Frozen liver samples were homogenized in ice-cold 150 mM Tris-HCl buffer (pH 7.4) of 1:10 wt/v ratio. Aliquots were prepared for the purpose of biochemical markers determination.

Antioxidant Status in Liver

Glutathione (GSH) content was determined by analyzing liver homogenates, according to the method of Van Dooran et al. The assay depends on measuring yellow 5-thiol-2-nitrobenzoate absorbance at 412 nm. Glutathione-S-transferase (GST) activity was determined using the method of Habig et al. GST catalyzes the conjugation of GSH thiol group with 1-Chloro-2,4-dinitrobenzene (CDNB), which can be measured by determining the increase in absorbance at 340 nm. For determination of catalase (CAT) activity, a method by Aebi was followed. CAT decomposes hydrogen peroxide ($H_2O_2$) to oxygen and water; therefore, the activity of CAT was evaluated according to by the exponential decomposition of $H_2O_2$ at 240 nm. Results are expressed in terms of units/mg of protein. A method by Nandi and Chatterjee was followed to assay superoxide dismutase (SOD) levels in liver homogenates. This method utilizes the inhibitive ability of SOD on autooxidation of pyrogallol (1,2,3-benzentriol) at alkaline pH. A method by Hillefass et al was used to determine myeloperoxidase (MPO) activity by measuring peroxidase activity of MPO that catalyzes oxidation of peroxide. The amount of MPO required to degrade 1 µM of peroxide/min describes one unit of MPO. Peterson modified-Lowry's method was used to evaluate total protein content in liver homogenates, to eliminate any interfering substances through deoxycholate-trichloroacetic acid protein precipitation step (Peterson, 1977). UV-160-Shimadzu recording spectrophotometer was used to record absorbances. Malondialdehyde (MDA) level was assayed spectrophotometrically by measuring the product of MDA reaction with thiobarbituric acid (TBA), a pink complex, at 535 nm (Mihara and Uchiyama, 1978). To determine liver homogenates content of protein carbonyl (P. carbonyl), a method by Reznick and Packer was followed. This method is based on the reaction of the carbonyl group with 2,4-dinitrophenylhydrazine (DNPH) to form a spectrophotometrically detectable hydrazone product at 370 nm. The results are expressed as nmol carbonyl group/mg protein, with molar extinction coefficient of 22000 M/cm.

TUNEL Assay and Immunohistochemical Staining

TUNEL assay was performed for the purpose of assessing apoptosis. 4 µm liver sections were deparaffinized and subjected to subsequent gradual hydration prior to staining. ApopTag peroxidase in Situ Apoptosis Detection kit was used according to the manufacturer's instructions (Serological Corporation, Norcross, USA). DNA fragmentation, a key indicator of apoptosis, is detected using this kit. Cell death was confirmed using M30 CytoDeath monoclonal antibodies by detecting the caspase-cleaved fragment of cytokeratin18.

For immunohistochemical staining, mounted sections were immersed in sodium citrate buffer (0.1 M, pH 6) and placed in a water bath for 15 minutes to unmask antigen epitopes. Afterwards, sections were incubated with 0.3% $H_2O_2$ in methanol, to block nonspecific binding to endogenous peroxidase. Sections were incubated overnight at 4° C. with rabbit anti-rat primary antibodies, anti-COX-2, anti-iNOS, anti-NF-kB-P65, and anti-Ki-67; in addition to M30 CytoDeath, monoclonal ED-2 anti-rat antibody, and polyclonal anti-rabbit antibodies, anti-GST-p and anti-p-TNFR. After incubation, slides were washed with PBS and incubated with polyvalent biotinylated goat-anti-rabbit, a secondary antibody, for 10 minutes at room temperature (1:200 dilution). Universal LSAB kit and DAB plus substrate kit were both used to perform standard staining protocol. Hematoxylin was used in additional counter-staining. Slides were observed under an Olympus DP71 optical microscope, and tissue images were obtained. Ten fields were randomly selected to quantify positive cells, in individual samples (400×). Color image processor was used to count GST-p foci more than 15 cells.

Histone Deacetylase Activity (HDAC) Assay

HDAC Colorimetric Assay Kit (Millipore Corporation, 28820 Single Oak Drive, Temecula, Calif. 92590, Catalog number: 17-374) was used to measure HDAC activity in liver homogenate.

Determination of Tumor Necrosis Factor-α (TNF-α)

TNF-α level in serum was quantitatively measured using Enzyme-Linked Immunosorbent Assay (ELISA), according to the manufacturer instructions (ELISA kits (R&D Systems), Minnesota, USA. Results are presented in picograms/milligrams.

Cell Culture

HepG2, were cultured in RPMI 1640 medium (HyClone, USA) and 1% of 100 U/ml penicillin and 100 ug/ml streptomycin (Sigma, USA) supplemented with 10% fetal bovine serum (Sigma, USA) at 37° C. in a humidified 5% $CO_2$ atmosphere. Cells were sub-cultured each 4-6 days using trypsin 0.25% (Hyclone, USA).

Cell Viability Assay

HepG2 cells were seeded in 96-well plates at the density of 10000 cells/well and grown in 100 uL of complete growth medium. Complete growth medium was replaced by serum-free medium after cells were allowed to attach for 24 hours; after which cells were incubated for at least 12 hours. Cells were incubated for 24 hours after treatment with various concentrations of safranal (1 mM, 0.3 mM, 0.1 mM, 0.03 mM, 0.01 mM) prepared from 10 mM stock solution. After incubation period, viability of HepG2 cells was assessed using CellTiter-Glo luminescent cell viability assay kit according to manufacturer's instruction (Promega, USA).

Caspase-3 and -7 Assay

HepG2 cells were seeded in 96-well plates at the density of 10000 cells/well and grown in 100 uL of complete growth medium. Complete growth medium was replaced by serum-free medium after cells were allowed to attach for 24 hours; after which cells were incubated for at least 12 hours. Cells were incubated for 48 hours after treatment with various concentrations of safranal (1 mM, 0.7 mM, 0.5 mM) prepared from 20 mM stock solution. After incubation period, caspase-3 and -7 activities were measured using Caspase-Glo 3/7 luminescent assay kit according to manufacturer's instruction (Promega, USA).

Western Blotting

In 100 mm plates, HepG2 cells were seeded at a density of $2 \times 10^4$ in complete growth medium. Cells were allowed to attach for 24 hours, after which complete growth medium was replaced by serum-free medium. Cells were treated with safranal at a concentration of 1 mM (20 mM stock). Plates were incubated for 6, 12, 24, and 48 hours in a humidified 5% $CO_2$ atmosphere at 37° C. At indicated times, 1 mL of cell supernatant was obtained from each plate and was stored at −80° C. for further analysis by ELISA. After which whole cell lysates were prepared. Bicinchoninic acid (BCA) assay (Sigma-Aldrich, USA) was used to determine concentration of protein. Thirty μg of protein were loaded onto 10% SDS polyacrylamide electrophoresis gels. The gels were transferred onto nitrocellulose membranes prior to immunodetection processing with anti-p-IkB-alpha, anti-H2AX (Cell Signaling Technology, USA), and with anti-rabbit IgG peroxidase conjugated secondary antibodies. Immunodetection was performed using Amersham ECL select western blotting detection reagent kit (GE healthcare life science, UK) and C-DiGit chemiluminescent western blot scanner (LI-COR) and image capturing software, Image Studio Digits.

ELISA

Supernatant of safranal-treated cells were used to investigate the effect of safranal on IL-8 secretion level. Human IL-8 ELISA Kit (EZHIL8, Millipore, USA) was used according to manufacturer's instructions. Absorbance was recorded at 450 nm with background subtraction at 570 nm using a microplate reader (Biotek, Winooski, Vt., USA).

Statistical Analysis

One-way analysis of variance (ANOVA) of our data was carried out using SPSS statistical program version 18 (SPSS Inc., Chicago, Ill., USA). Upon detection of significant differences by ANOVA, Dunnett's t test was performed to analyze the differences between means of the treated and control groups.

Results

Safranal Possesses Antioxidant Properties

The antioxidant status in the liver and the effects of safranal on markers of oxidative stress were evaluated in vivo. In group 3 (HCC) levels of MDA, CAT, SOD, MPO, and P.carbonyl were significantly elevated compared to control levels, whereas the activity of SOD decreased. Such changes in oxidative stress markers can be attributed to DEN-2AFF-induced hepatic oxidative stress and damage. Dramatic change in oxidative stress markers was not evident in the protective groups (groups 4-5) that were treated with low/high doses of safranal after to DEN exposure, in comparison to the control group. Administration of safranal alone (group 2) had did not alter the activity levels of any of those oxidative stress markers and stayed at control levels.

Table 1 shows the summary of the effects of safranal on oxidative stress markers. Values are expressed as mean±SEM of eight rats per group. Concentration is expressed as nmol/mg protein for MDA, P.Carbonyl, and GSH. Activity is expressed as unit/mg protein for CAT, SOD and GST. Activity is expressed as milliunit/mg protein for MPO. Significance was determined by one-way analysis of variance followed by Dunnett's t test: $^a P<0.001$ vs. normal group:

TABLE 1

| Groups | MDA | P.Carbonyl | CAT | SOD | MPO |
|---|---|---|---|---|---|
| Control | 0.66 ± 0.02 | 1.51 ± 0.04 | 144.12 ± 0.65 | 4.07 ± 0.04 | 33.55 ± 0.31 |
| Safranal (Saf) | 0.64 ± 0.02 | 1.52 ± 0.03 | 143.75 ± 1.2 | 4.05 ± 0.09 | 32.61 ± 1.61 |
| HCC | 0.87 ± 0.02$^a$ | 2.16 ± 0.06$^a$ | 167.14 ± 4.47$^a$ | 3.38 ± 0.06$^a$ | 49.92 ± 4.5$^a$ |
| HCC + Saf LD | 0.61 ± 0.02 | 1.61 ± 0.06 | 141.38 ± 0.91 | 4.02 ± 0.18 | 27.47 ± 1.77 |
| HCC + Saf HD | 0.63 ± 0.03 | 1.45 ± 0.06 | 145.4512 ± 4.57 | 3.96 ± 0.13 | 31.54 ± 2.4 |

Safranal Inhibits DEN-Induced FAH Formation and GST-p Expression

Upon histological examination of liver sections taken from animals treated with DEN-2-AAF, large hepatocellular nodules—irregular in morphology and pale in color, with larger nuclear/cytoplasmic ratio—were observed. Such alteration is a classical representation of foci of altered hepatocytes (FAH) that emerges prior to the development of HCC. Nonetheless, treatment with safranal alone abolished such hepatocellular nodules almost completely; in addition, the number and size of these nodules were remarkably decrease in number and size, in the protective groups treated with low/high doses of safranal (FIGS. 2A1-2A5).

Figure 2C:
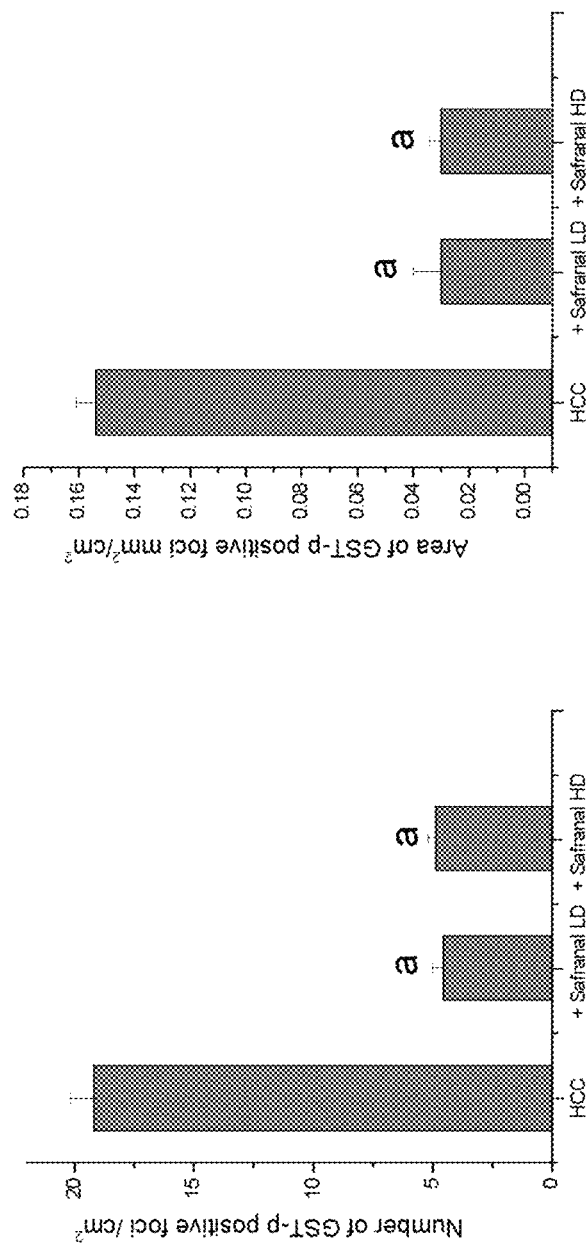
FIG. 2C illustrates a quantitative analysis of GST-p-positive foci. The number and area of GST-p-positive foci was reduced in saffron based biomolecules-treated rats. Significance was determined by one-way analysis of variance followed by Dennett's t test: $^{a}$P<0.001 vs. DEN group.

As a reliable liver tumor-biomarker that is expressed throughout hepatocarcinogenesis, placental glutathione s-transferase (GST-p) expression was evaluated. The number of GST-p positive foci and their area per cm$^2$ were significantly increased in liver sections taken from animals treated with DEN-2-AAF; which is consistent with hepatocarcinogenesis. However, safranal treatment alone (group 2) did not induce formation of such foci; in addition, safranal treatment after DEN exposure significantly reduced the number of GST-p positive foci and the area/cm$^2$ (groups 4-5) (FIGS. 2B1-2B5, GST-p panel). Foci larger than 15 cells were measured with a color image processor. Calculations of the number of foci and their area/cm$^2$ were carried out as well. (FIG. 2C).

Proliferation and Apoptosis Mediate Safranal-Induced Inhibition of HCC

Elevated levels of Ki-67 is a key feature in normal proliferating cells; however, its overexpression is consistent with tumorigenesis. This is evident in DEN-2AAF-treated animals liver sections (group 3) that had shown a significant increase in Ki-67-positive cell numbers compared to control group. Treatment with safranal alone did not induce a significant change in the number of Ki-67-expressing hepatocytes (group 2). Pre-treatment with low/high doses of safranal in animals exposed to DEN, on the other hand, dramatically reduced the number of Ki-67 positive cells (group 4-5) (FIGS. 3A1-3A6; Ki67 panel).

M30 CytoDeath antibody was used to assess early apoptosis by specifically detecting a fragment of cytokeratin 18 cleaved by caspase. For the detection of DNA fragmentation caused by apoptosis, TUNEL assay was also performed. In group 2, in which all animals were treated with safranal only, the number of both TUNEL-positive cells (FIGS. 3C1-3C6; TUNEL panel) and M30 CytoDeath-positive cells (FIGS. 3B1-3B6; M30 panel) did not exhibit a notable change, compared to control group. However, a significant increase in the number of TUNEL-positive cells and M30 Cyto-Death-positive cells was observed in DEN-2AAF-treated animals liver sections (group 3), compared to that of the control group. Nonetheless, pre-treatment with low/high doses of safranal induced up-regulation of apoptosis in animals exposed to DEN; and their liver sections shown a significant increase in the number of both TUNEL- and M30 CytoDeath-positive cells when compared to group 3.

Safranal's Inhibition of HCC is Mediated Through Inflammation

Figure 4A:
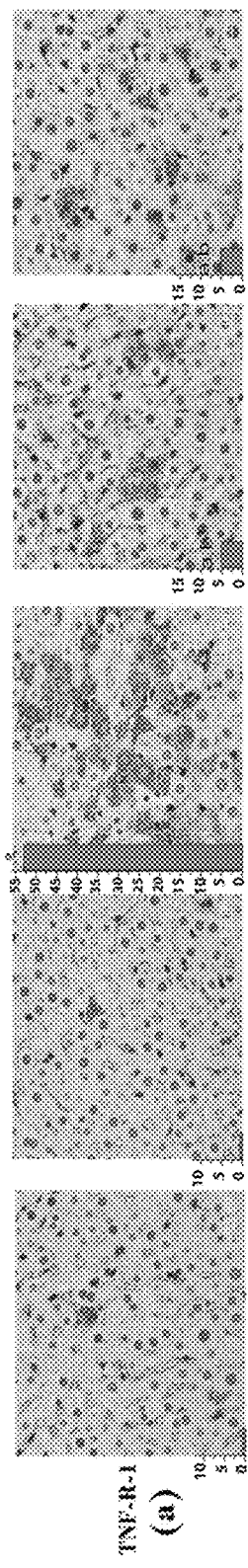
FIGS. 4A-4E illustrate the effects of safranal on inflammation.
Figure 4B:
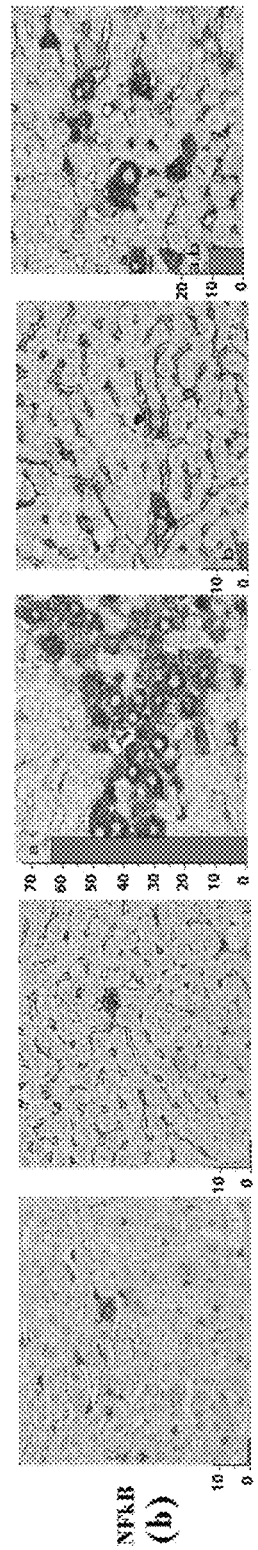
Figure 4C:
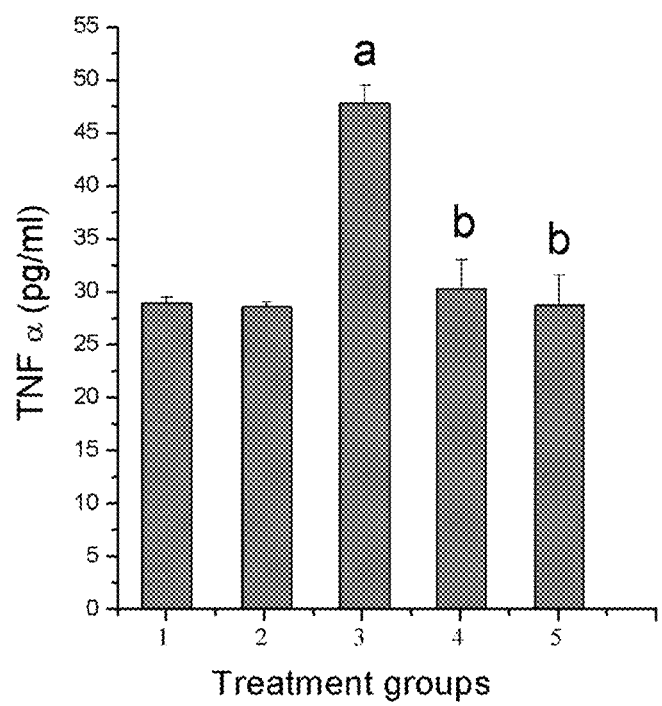

Treatment with DEN-2-AAF caused a dramatic increase in the number of p-TNF-R1 positive cells. However, pre-treatment with low/high doses of safranal caused a highly significant decrease in the number of p-TNF-R1 positive cells in liver sections of DEN-2-AAF-treated animals (group 4-5), in comparison to that of the HCC group. Notably, treatment with safranal alone exhibited a change of no significance on the number of p-TNF-R1 positive cells, when compared to the control group (FIG. 4A). ELISA assay was used to evaluate TNF-α level of expression (FIG. 4C). Treatment with DEN-2AAF induced a notable elevation in the expression level of TNF-α (group 4) when compared to control group. Notably, treatment with safranal alone had no significant impact on the activity of TNF-α (group 2) in comparison to control group. However, a significant reduction in TNF-α expression was observed upon treatment with low/high doses of safranal after DEN exposure (group 4-5).

DEN-2-AAF treatment also caused a significant increase in levels of COX-2 and iNOS expression. Reported in Table 2 are the effects of safranal on the numbers of ED-1, ED-2, iNOS, COX-2 positive cells. Values are expressed as mean±SEM of eight rats per group. Number of positive cells/field. Significance was determined by one-way analysis of variance followed by Dennett's t test: $^a$P<0.001, $^c$P<0.01 vs. normal group 1; $^b$P<0.001, $^d$P<0.01 vs. HCC group:

TABLE 2

| Groups | ED-1 | ED-2 | iNOS | COX-2 |
|---|---|---|---|---|
| Control | 44.87 ± 0.88 | 39.0 ± 0.67 | 0.87 ± 0.02 | 0.59 ± 0.04 |
| Safranal (Saf) | 44.33 ± 1.52 | 39.30 ± 1.77 | 0.87 ± 0.04 | 0.58 ± 0.04 |
| HCC | 111.4 ± 4.55$^a$ | 78.00 ± 0.73$^a$ | 53.17 ± 2.13$^a$ | 37.78 ± 2.38$^a$ |
| HCC + Saf LD | 59.19 ± 2.0$^{a\&b}$ | 46.75 ± 3.04$^b$ | 5.09 ± 0.26$^{a\&b}$ | 2.15 ± 0.38$^b$ |
| HCC + Saf HD | 49.84 ± 2.28$^b$ | 46.44 ± 3.12$^b$ | 2.57 ± 0.30$^b$ | 6.91 ± 1.09$^{a\&b}$ |

Pre-treatment with low/high doses of safranal almost completely abolished the effects of DEN-2-AAF in groups 4-5 in comparison to control groups. Additionally, DEN exposure caused a significant increase in the NF-kB-p65 positive cells that were highly expressed in Kupffer cells and around the central vein. Pre-treatment with low/high doses of safranal significantly reduced the number of NF-kB-p65-positive cells, in comparison to that of the HCC group (FIG.

Figure 4D:
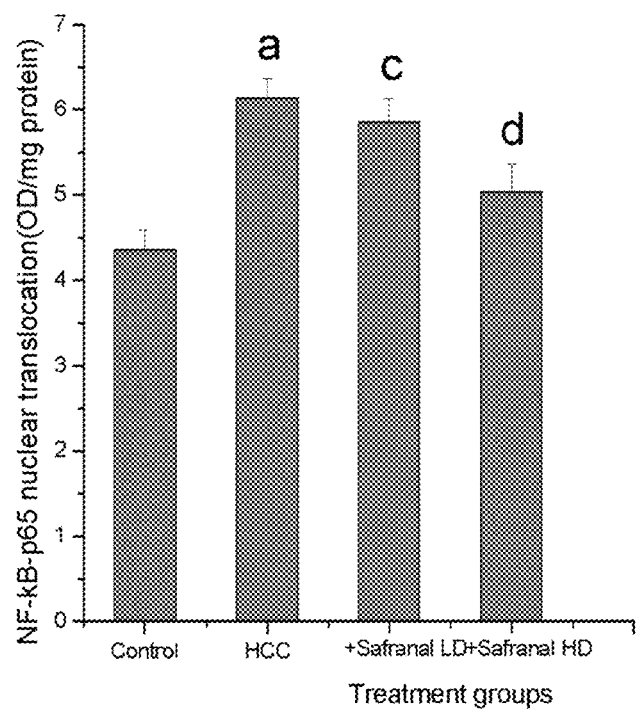

4B). In addition, a parallel decrease in NF-kB-p65 level in nuclear extracts was observed in animal groups pre-treated with safranal, indicating that safranal is able to inhibit NF-kB translocation to the nucleus; hence, attributing the anti-inflammatory effect of safranal to blocking of NF-kB signaling in this particular HCC model (FIG. 4D).

ED-1 was used as a cellular marker for assessing macrophages activity. DEN-2-AAF treated animals exhibited a dramatic overexpression of macrophages, which was observed in obtained liver sections (group 3). However, pre-treatment with low/high doses of safranal eliminated such up-regulation (groups 4-5). Notably, treatment with safranal alone had no significant impact on macrophages activity in group 2 when compared to control group (Table 2). Activity of Kupffer cells, resident macrophages, was assessed with a cellular marker ED-2. DEN-2-AAF treated animals demonstrated a significant increase in the expression of Kupffer cell marker, which was observed in obtained liver sections. Pre-treatment with safranal at low/high doses dramatically reduced the number of Kupffer cells on DEN-2AAF treated groups (groups 4-5), compared to the control group. However, treatment with safranal alone (group 2) had no effect on the number of Kupffer cells compared to control (Table 2).

Safranal Inhibited HDAC in Liver

Figure 4E:
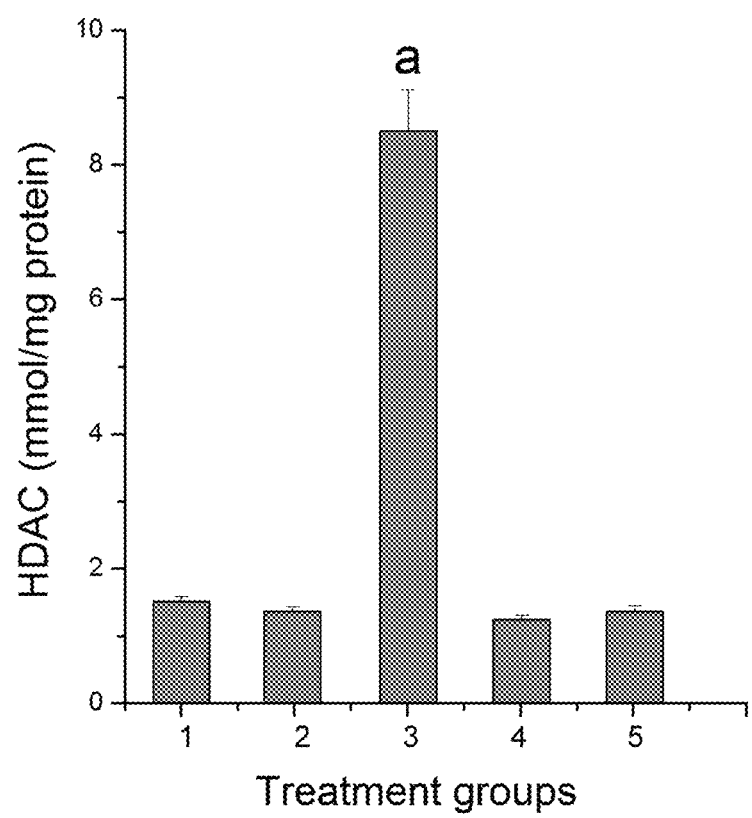

Activity levels of HDAC were determined in vivo. DEN-treated animals (group 3) exhibited a highly significant increase in HDAC activity. Nonetheless, pre-treatment with low/high doses of safranal (groups 4-5) restored HDAC activity to the normal range (FIG. 4E). Treatment with safranal alone (group 2) did not change HDAC activity compared to control.

In Vitro Analyses

Figure 5A:
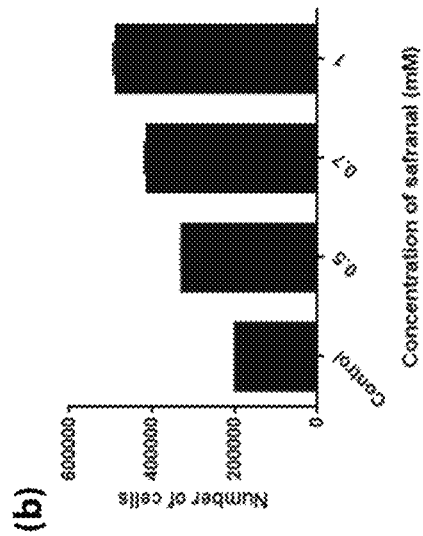
FIGS. 5A-5D illustrate an In vitro analysis.
Figure 5B:
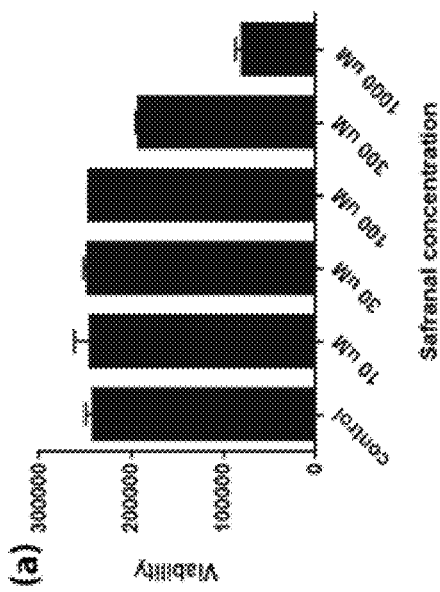
Figure 5C:
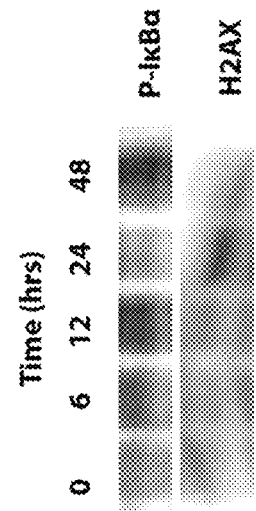

In vitro analysis was performed to highlight the anticancer effects of safranal on HepG2 cells. Various concentrations of safranal (0.01, 0.03, 0.1, 0.3, 1 mM) were used to treat the cells for 24 hours. Cell viability was assessed using Cell-Titer-Glo kit. Safranal exhibited a significant dose-dependent reduction of HepG2 cells viability. At a concentration of 1 mM was able to reduce cell viability by almost 70% (FIG. 5A). Post treatment with various concentrations of safranal for 48 hours, significant increase in caspase-3 and -7 activities was noted at a concentration of 1 mM (FIG. 5B). A dramatic decrease in IL-8 secretion as early as 6 hrs. was also reported when HepG2 cells were treated with various concentrations of safranal (FIG. 5C).

Figure 5D:
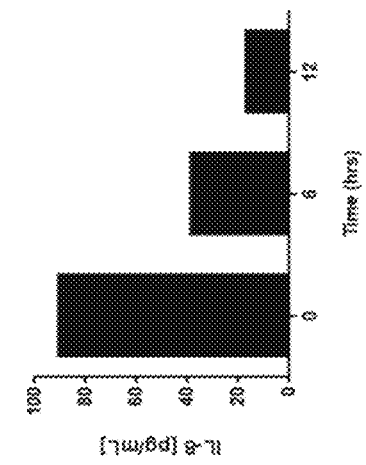

Level of p-IkB protein has been transiently decreased after treatment with safranal starting at 24 hours (FIG. 5D). To examine whether DNA-damage mediates safranal's anticancer effect, protein level of p-H2AX, a sensor for DNA double strand breaks, was analyzed by western blotting. HepG2 cells showed a remarkable induction of p-H2AX at 24 hours of safranal's treatment (FIG. 5D).

Discussion

The results reported in this study nominate safranal as a promising candidate in cancer chemoprevention via acting against early hepatic preneoplastic events. High expression level of GST-P is normally associated with carcinogenesis and hence is a reliable marker for experimental hepatocarcinogenesis in rats. This study demonstrated the dramatic reduction in both the number and area/$cm^2$ of GST-P positive foci upon pre-treating DEN-induced HCC groups with safranal; which was consistent with a visible reduction in FAH formation, a preneoplastic lesion that promotes HCC development.

Sustained proliferative signaling and the impediment of apoptosis are key physiological conditions in cancer cells that supports tumor initiation and progression. As it is strictly expressed during proliferation, Ki-67 was used in this study to assess cellular proliferation. Clear antiproliferative effect of safranal was shown in all pre-treated DEN-induced rats, where expression of Ki-67 was significantly reduced. Safranal's pro-apoptotic activity was also documented as reflected in the increased number of TUNEL- and M30 CytoDeath-positive cells; indicators of DNA fragmentation and early apoptosis, respectively. These findings are consistent with published literature reporting the anti-proliferative and pro-apoptotic effects of safranal in alveolar human lung and prostate cancer cell lines. Thus, the present results indicate that the safranal-induced inhibition of hepatic neoplasia was mediated with both up-regulation of apoptosis and down-regulation of cellular proliferation.

Many experimental and clinical studies have highlighted the supportive role of oxidative stress in human carcinogenesis by altering many aspects of cancerous cells; which is evident in many types of cancers such as colorectal, breast, prostate cancers, as well as in melanoma. Oxidative stress is similarly implicated in hepatocarcinogenesis, where significant elevation of ROS activities along with drastic reduction in anti-oxidative scavenging activities are well documented. In this study, DEN-induced HCC animals showed elevated levels of oxidative stress markers, MDA and P. Carbonyl; in addition to altered levels of antioxidants activity, SOD and CAT. Interestingly in this study, safranal reduced overproduction of MDA and P. Carbonyl and restored normal levels of SOD and CAT antioxidants activities in protected animal groups. It also upregulated H2AX protein level.

Chronic inflammation plays a role in establishing a permissive environment for cancer development by triggering the activation pattern of macrophages and Kupffer cells. Such inflammation also promotes unbalanced production of pro-inflammatory mediators such as nitric oxide, TNF-α, and many transcription factors including NF-κB. The present study demonstrates the great efficacy by which safranal pre-treatment was able to eliminate inflammation in DEN-induced HCC model by restoring normal hepatic MPO levels, a marker of neutrophil infiltration, reducing the number of both hepatic ED1- and ED2-positive macrophages, and inhibiting TNF-mediated inflammatory pathway via reducing the content of TNF-α and the number of p-TNF-R1 positive cells. TNF-α tumor-promoting action is attributed to its involvement in TNFR1 activation, in addition to mediating proliferation and inflammation.

Elevated levels of COX-2 and iNOS enzymes are known to be associated with many malignant tumors through promoting cell growth and disrupting cell death machinery. Therefore, inhibiting both of these enzymes can subsequently promote the inhibition of tumor growth; as it has been reported in many studies, and demonstrated in this study as well. NF-κB plays a major role in cancer promoting setting by modulating expression of many genes via nucleus oxidative stimuli. This modulation in gene expression is responsible for altered inflammatory responses, up-regulation of COX-2 and iNOS, promoting cell proliferation, and inhibiting cell death. NF-κB has been described as pro-carcinogenic in genetically modified HCC mouse models and in DEN-induced HCC. The present findings showed the ability of safranal pre-treatment to reverse induced overexpression and nuclear translocation of NF-kB-p65 subunit in DEN-induced rats. We then tested whether or not a similar safranal-dependent NF-κB inactivation persists in vitro. Thus, the presence of the phosphorylated form of the Ikappa-B protein (p-IkB) was evaluated by western blotting. Once phosphorylated, IkB is known to be rapidly degraded thereby allowing activation of the NF-kB complex through its translocation into the nucleus. Indeed, we found an early decrease of p-IkB protein levels in cells treated with safranal, confirming an early inactivation of NF-kB (FIG. 5D). The decrease of Kupffer cells and neutrophils reported here seems to be associated with an early inactivation of NF-kB signaling pathway, as reflected in the early in vitro inhibition of p-IkB and IL-8 (FIG. 5D). Collectively, findings reported here suggest that safranal's anti-cancer properties could be could be attributed to their anti-inflammation activities through down-regulation of NF-κB, COX-2 and iNOS expression levels and reduction of both TNF-α and its receptor.

Many studies have reported the role of histone deacetylase (HDAC) in modulating gene expression by packing DNA tightly around histones, making DNA inaccessible through removing acetyl groups from an ε-N-acetyl lysine amino acid on a histones. An altered HDAC profile has been reported in several diseases, and associated with development and progression of many cancers; including HCC, in which overexpression of HDAC could be linked to aggressive forms. In addition, HDAC activity level in HCC patient that undergone liver resection serves as an independent prognostic factor. Hence, inhibiting HDAC activity could play a role in slowing down tumor development and progression. This is clearly demonstrated in the ability of HDACi to trigger apoptosis, in both hematological and solid cancers through transcription dependent and independent manner. HDACi pro-apoptotic activity could be attributed to its ability to promote cell cycle arrest and to induce expression of pro-apoptotic genes, in addition to causing DNA damage through several mechanisms. Our findings reported the significant effect of safranal pre-treatment on inhibiting increased HDAC expression in DEN-treated HCC model and restoring it to control level. Taken together, these findings suggest that anti-proliferative and pro-apoptotic properties of safranal could be attributed, at least in part, to its inhibitory ability of HDAC overexpression in cancerous cells.

In conclusion, findings reported in this study clearly showed the great efficacy of safranal in preventing HCC in DEN-treated rats, which can nominate safranal as a potential chemopreventive drug against HCC. Safranal treatment was efficient in inhibiting FAH formation in DEN-induced HCC models, restoring the antioxidant normal levels and reducing all tested oxidative stress markers. In addition, significant decreases in the activity of inflammatory markers, COX-2, iNOS, NF-κB, TNF-α and its receptor p-TNF-R1 were observed in DEN-induced HCC model pre-treated with safranal. Moreover, pre-treatment with safranal induced a reduction in the number of Kupffer cells and macrophages. These findings were also confirmed in vitro by utilizing the human hepatoma cell line "HepG2" where safranal has consistently demonstrated pro-apoptotic and anti-inflammatory properties.

Definitions

As used in this description and the accompanying claims, the following terms shall have the meanings indicated, unless the context otherwise requires:

As used herein, "treatment" is understood to refer to the administration of a drug or drugs to a patient suffering from cancer.

As used herein, the term "pharmaceutically acceptable salt" of a compound is understood to refer to conventional acid-addition salts or base-addition salts that retain the biological effectiveness and properties of the compound and are formed from suitable non-toxic organic or inorganic acids or organic or inorganic bases. Acid-addition salts include, for example, those derived from inorganic acids, such as hydrochloric acid, hydrobromic acid, hydroiodic acid, sulfuric acid, sulfonic acid, phosphoric acid, and nitric acid, and those derived from organic acids, such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and quaternary ammonium hydroxides, such as for example, tetramethyl ammonium hydroxide.

What is claimed is:

1. A method of reducing carcinogenesis of liver cancer in a human or animal, comprising administering an amount of safranal to the human or animal subject,
    wherein the human or animal subject suffers from hepatic oxidative stress and exhibits elevated levels of one or more markers associated with liver tumorigenesis selected from the group consisting of: malondialdehyde (MDA), catalase (CAT), superoxide dismutase (SOD), myeloperoxidase (MPE), and serum protein carbonyl (P. carbonyl), and
    wherein the amount of safranal is from 15 mg/day per kg body weight to 60 mg/day per kg body weight of the subject.

2. The method of claim 1, where the subject suffers from hepatic inflammation.

3. The method of claim 1, where the amount of safranal is from 20 mg/day per kg body weight to 50 mg/day per kg body weight of the subject.

4. The method of claim 1, where the amount of safranal is from 25 mg/day per kg body weight to 45 mg/day per kg body weight of the subject.

5. A method of reducing carcinogenesis of a liver cancer in a human or animal subject, comprising:
    monitoring the level of a liver cancer marker, and
    administering an amount of safranal to the human or animal subject, where said amount is effective to maintain a normal level of the liver cancer marker,
    wherein the human or animal subject suffers from a liver condition conducive to liver cancer,
    wherein the amount of safranal is from 15 mg/day per kg body weight to 60 mg/day per kg body weight of the subject, and
    wherein the liver cancer marker is an oxidative stress marker selected from the group consisting of: malondialdehyde (MDA), catalase (CAT), superoxide dismutase (SOD), myeloperoxidase (MPO), serum protein carbonyl (P.carbonyl), and combinations thereof, or the liver cancer marker is an inflammation marker selected from the group consisting of: tumor necrosis factor alpha (TNF-α), cyclooxygenase-2 (COX-2), i-nitrous oxide synthase (iNOS), and combinations thereof.

6. The method of claim 5, where the liver condition is selected from the group consisting of hepatitis B, hepatitis C, cirrhosis, non-alcohol fatty liver disease, iron overload, and exposure to environmental carcinogens.

7. The method of claim 5, where the amount of safranal is from 20 mg/day per kg body weight to 50 mg/day per kg body weight of the subject.

8. The method of claim 5, where the amount of safranal is from 25 mg/day per kg body weight to 45 mg/day per kg body weight of the subject.

9. A method of reducing carcinogenesis of a liver cancer in a human or animal subject, the cancer resulting from exposure to a carcinogenic agent, the method comprising administering to the human or animal subject an amount of safranal, wherein the amount of safranal is from 15 mg/day per kg body weight to 60 mg/day per kg body weight of the subject.

10. The method of claim 9, where the carcinogenic agent is selected from the group consisting of a chemical agent, a pharmaceutical agent, a form of radiation, and combinations thereof.

11. The method of claim 9, where the amount of safranal is from 20 mg/day per kg body weight to 50 mg/day per kg body weight of the subject.

\* \* \* \* \*